US006322814B1

(12) United States Patent
Miller

(10) Patent No.: US 6,322,814 B1
(45) Date of Patent: Nov. 27, 2001

(54) MANUFACTURE OF AND USES FOR LOW MOLECULAR WEIGHT AGARS AND AGAROIDS

(76) Inventor: Ian James Miller, P.O. Box 30 366, Lower Hutt (NZ)

( * ) Notice: Subject to any disclaimer, the term of this patent is extended or adjusted under 35 U.S.C. 154(b) by 0 days.

(21) Appl. No.: 09/456,017

(22) Filed: Nov. 29, 1999

Related U.S. Application Data

(63) Continuation of application No. 08/687,598, filed as application No. PCT/NZ94/00057 on Jun. 9, 1994, now abandoned.

(30) Foreign Application Priority Data

Mar. 4, 1994 (NZ) ...................................................... 260029

(51) Int. Cl.[7] ...................................................... A61K 9/16
(52) U.S. Cl. .................. 424/484; 424/78.02; 424/78.05; 424/78.06; 424/78.07; 424/195.17; 424/400; 424/409; 424/485; 424/488; 536/114; 514/24; 514/64; 514/54
(58) Field of Search ............................ 536/114; 523/105, 523/122; 426/72, 311; 424/405, 406, 484, 485, 488, 442, 439, 400, 401, 78.02–78.07, 409, 195.17; 514/24, 64, 54

(56) References Cited

U.S. PATENT DOCUMENTS 2,624,727 * 6/1953 Le Gloahec ........................ 536/114
3,342,612 * 9/1967 Foster et al. ........................ 536/114

FOREIGN PATENT DOCUMENTS

0570252 * 11/1993 (EP) .

* cited by examiner

Primary Examiner—Neil S. Levy

(57) ABSTRACT

A process is claimed whereby an aqueous solution of agar, in which most (ideally all) 4-linked residues consist of 3,6-anhydro-L-galactose, is subjected to partial acid hydolysis and upon neutralization following the time appropriate for the chosen conditions, a low strength gel is obtained, from which, contrary to expectations, a polyagarobiose can be obtained by freeze-thawing and straining, thereby eliminating undesirable agaroid materials without the appropriate 3,6-anhydrogalactosyl content. The appropriate time of hydrolysis depends on initial gel strength, pH, counterion concentration and temperature. As an example, agar (gel strength 700 $g/cm^2$, made to 1.86% solution) pH 3.25, counterion citrate (360 mg/L) at 96° C. requires 25 minutes to yield a material with an eventual gel stregth (1.5% solution) of 40 $g/cm^2$. A stabilized product can be prepared by reducing terminal anhydrogalactosyl residues with sodium borohydride. The resultant products are useful for preparing gels for application to the skin, such as massage gels, as skin moisturizers, or as carriers of other active ingredients, such as pharmaceuticals able to be applied through the skin.

12 Claims, No Drawings

MANUFACTURE OF AND USES FOR LOW MOLECULAR WEIGHT AGARS AND AGAROIDS

This application is a Continuation of U.S. patent application Ser. No. 08/687,598, now abandoned derived from International Application No: PCT/NZ94/00057 dated Jun. 9, 1994.

This invention relates to methods of making agars with very low gel strengths, and the discovery of uses for these materials.

According to the US Pharmocopeia, agar is a hydrophilic colloid which can be extracted from certain seaweeds of the Rhodophyceae. Its characteristic property is that it is insoluble in cold water, and if 1.5% parts by weight are dissolved in hot water, on cooling it forms a firm gel. Agar is generally considered to be a mixture of agarose and agaropectin. Idealised agarose is a polymer with alternating 3-linked β-D-galactosyl residues and 4-linked α-3,6-anhydro-L-galactosyl residues, which can also be thought of as polyagarobiose, and gelation is generally held to arise through the formation of double helices between agarobiose units (Rees, 1969). Agar generally contains a number of agarose precursor units, where the 4-linked residues contain L-galactose-6-sulphate. These 6-sulphated residues cannot form double helices, and hence when these units arise in agar, it is generally held that helix formation terminates, the strands branch, and may form further double helices when strands with appropriate agarobiosyl units can meet. The resultant gel is, accordingly, a large interwoven network. If there are too many L-galactose-6-sulphate units, the amount of double helix structure is too small, and the gel strength weakens. Since L-galactose-6-sulphate units can be converted to anhydrogalactosyl units by treatment with alkali, alkali treatment of agar, or agar bearing seaweeds, is commonly practised in order to improve gel strength (Armisen 1987).

Alkali treatment of agar to improve gel strength is well known to those familiar with the art, and the literature contains a number of procedures. For the purposes of this invention, we define an alkali treatment as "rigorous" if if a repeat of the treatment or of a standard alternative alkali treatment to the resultant agar leads to no significant decrease in level of sulphate ester.

Agar is generally used industrially because of its rather unusual gelling properties, and the gel strength of an industrial agar of 1.5% concentration generally lies between 600–1100 $g/cm^2$. An important feature of an agar gel is the property of syneresis, whereby when pressure is applied to it, water is squeezed from the gel. Accordingly in some cases when a weaker binding force is required and the option of using less agar might lead to excess syneresis, an agar which has had its gel strength reduced might be used as increasing the agar content reduces the tendency towards syneresis. The manufacture of a partially hydrolysed agar for this purpose has been proposed (Kojima et al 1993). Of particular interest regarding this material is the proposed means of dehydratng the gel, as shown by the following quote: "when an agar of low gel strength is interposed between dehydrating cloths and pressurized, clogging occurs in the cloths and dehydration is not performed desirably. On the other hand, in the case of employing the freezing/denaturing process, an agar gel of a low gel strength does not have an orderly spongy structure, and it is caused to flow out with water." Accordingly these workers proposed to prepare a low gel strength agar and isolate it by evaporating off water, with the option of alcohol precipitation from concentrated solutions.

It is generally held to be not possible to make an idealized agarose, as there is always some residual sulphate ester, but it becomes clear from the above theory that if sufficient sulphate ester is removed, and sufficient hydrolysis is performed to shorten the polyagarobiose molecules, strands of shorter double helices may be formed with no defects in their structure. Although the constituent analyses may be little different from a low gel strength agar, significant differences in properties of the material should be expected, since on the molecular level, there will be a minimum of interstrand connectivity, and the molecules will consist of rods of double helix. The purpose of this invention is to show that these expectations can be met, although this invention is not intended to be dependent on the validity of the theory outlined above.

What we have found is that provided there is sufficiently low levels of anionic content arising from sulphate ester, and if the hydrolysis is carried out for a sufficient length of time, what is obtained is a material which behaves in solution like a thick paste. While normal agar, after freeze-thawing, is recovered as leathery spongy-like lumps corresponding to the original lumps of agar, and weak gel-strength agar does not denature at all well, leaving a material with insufficient strength to enable it to be easily recovered, if the product of this invention is freeze-thawed, the polyagarobiose units, assumed to be in the rod-like configuration, form a coarse fibre-like precipitate which can be recovered by straining the water through a gauze. The fibrous material is able to be further dewatered by squeezing it for a few minutes in a filter cloth and the precipiate is sufficiently firm that clogging does not occur. Although the material of this invention does not have to be purified this way, it is characteristic of the material of this invention that it can undergo such a freeze-thawing process. This clearly differentiates it from the weak-gelling agar in the prior art, for which the freeze-thawing process is unavailable.

Gel strengths are usually recorded in terms of the ability of a gel to support a force for 20 seconds. This material has zero rigidity, hence such a measurement would give a result of zero. We have, however, found it possible to differentiate between such virtually zero strength gels according to their resistance to flow, by placing the gel on a balance pan and penetrating the material with a 1 $cm^2$ plunger within a period of approximately 1 second. The maximum reading from the balance is recorded as a dynamic gel strength, and while it is somewhat arbitrary, it does separate very weak gels into two classes, namely those with such a dynamic gel strength of less than 10 $g/cm^2$, which are essentially thick flowing liquids, and those greater than 10 $g/cm^2$ by this method, in which some gel-like structure is progressively retained as the dynamic gel strength increases so that on stirring some gel-like lumps are retained.

A number of other agar bearing seaweeds give low gel strengths when extracted, but when treated with alkali following methods known to those practised in the art, give an agar with a higher gel strength. These initial weak gels tend to rupture, and in the limit of weakness flow as a sloppy gel. These initial weak gels generally consist of agar molecules which have high levels of anionic substitution, for example, sulphate ester, and the preparation of such materials are not the subject of this invention.

If, however, the agars from such seaweeds are treated according to the methods of this invention, that is they are subjected to rigorous alkali treatment followed by controlled acid hydrolysis, the resultant gels have a rather unusual creamy texture and with unusual water retention properties. The best gels for some of the purposes of this invention are gels which have a low gel strength specifically because of the lower molecular weight, and paradoxically are best prepared from high gel strength agars. The material of this patent is a low molecular weight agar with negligible amounts of 4-linked residues in any form other than as anhydrogalactosyl. It is characterized by forming an ultraweak gel with a very low gel strength, but which, on freeze-thawing, forms a readily collectible coarse fibre-like precipitate. Of special note is the absence in the 13CNMR spectrum of any significant signal at 67.9 ppm or at 101.3 ppm which would be due to L-galactose-6-sulphate.

There are already a number of thickeners and gels on the market which have a number of uses, particularly in the food industry, and the uses are generally based on water retention properties, gelling ability, emulsifying properties, and stabilizing properties. Many of these properties depend on the specific chemical nature of the colloid, and because the different agents have different properties, each find specific niche uses. Most of the colloids in current use either give viscous solutions, strong gels, or have chemical functional groups which specifically interact with other materials. While this may be useful for certain applications, it can be a disadvantage on other occasions.

The materials described in this invention are neutral non-interacting colloids with low gel strength and which have properties which are either difficult to obtain with other materials, or which will at least provide the public with a useful choice. There are a range of products with a narrow range of properties which depend on the origin of the material. Whereas the normal purpose of agars is to give a firm texture in the end result, to suspend materials or to hold them together, in other words the focus is generally on the solid components, the most common use envisaged for these materials is for carrying and releasing fluid, especially water and materials dissolved in it, in other words the focus is generally on the fluid it contains. It is for this reason that the gel is made deliberately weak, namely to make it easy for the controlled release of liquid.

The preferred material for many applications is a polymer with as little substitution as possible, and with the highest anhydrogalactosyl content, and this type of polymer is best obtained by hydrolysis of an agar of high gel strength under controlled acidic conditions. Acid hydrolysis is a well known method for degrading agar, and generally it has been used to determine the constituent sugar in agar. The essence of this invention is that it is possible to control such a hydrolysis, to prepare new materials suitable for use to which agar itself is far less suitable.

Alternative methods of obtaining the low gel strength polymer are available, however, and include oxidative degradation, fractionation of the polymer and also alkali treatment of the agaropectin molecules. A further method is to heat the moist solid in the presence of certain inorganic materials, which is a variation of the hydrolysis method. The acid hydrolysis is, however, the most readily controlled method of obtaining this material.

The starting material for the preparation of the low gel strength agars of this invention can also be specific seaweeds which produce relatively low gel strength agars naturally as a consequence of a naturally low molecular weight and/or excess sulphate ester. For these polysaccharides, rigorous alkali treatment is required, but the following acid hudrolysis may have to be carried out for a relatively short time. Without limit to the generality, these seaweeds may include certain Gracilaria species, especially those whose gel strength has otherwise been considered too weak to be of commercial interest, including as an example, but without limit on the generality, *Gracilaria secundata* which when extracted, even after rigorous alkali treatment yields an agar with a gel strength in the order of 35 g/cm$^2$, and also species from from the Ceramiaceae and Rhodomelaceae, where specific substitution on the resultant agar-type molecule may give properties of specific interest. Of particular interest is the presence of natural methylation. A specific example is the agar from *Euptilota formosissima*, which, following alkali treatment and extraction, has a gel strength up to 140 g/cm$^2$, and has the 6-hydroxyl group of the D-galactose units almost completely methylated, which in turn will give the material more hydrophobic properties. This agar, following short acid hydrolysis, gives a very low gel strength agar with the creamy nature, but the more hydrophobic nature of the agar gives this agar a different texture, and it should also be more useful for dispersing more hydrophobic components, such as oils and some flavours. A further example which demonstrates the key feature of this invention is the agar from *Curdiea coriacea*. The natural extract either does not gel, or it gels very weakly, but the weak natural gel, with its high level of 6-sulphate ester, cannot be easily purified by freeze-thawing and the material is unsuitable for the purposes of this invention. Following alkali treatment, a gel strength of well over 1000 g/cm$^2$ is readily obtainable, and following acid hydrolysis as described herein, a weak gel is again obtained, but this time on freeze-thawing it forms the coarse precipitate-like material which is easily recovered. This material has two methyl groups per agarobiosyl unit (Furneaux, Miller & Stevenson, 1990) and is even more suitable for dispersing hydrophobic materials.

The methylated agars employed here are naturally methylated. Synthetic alkylation is also possible (Guiseley, 1976) but this material differs from currently known natural materials in that alkylation also occurs at the 2-position of the 3-linked residue. It has been shown that such alkylation disrupts the double helix, and incidentally lowers the gelling temperature and the gel strength (Miller, Falshaw and Furneaux, 1994), and such materials are different from those of this invention.

The material can also be obtained from seaweeds which would normally produce agar with a high gel strength, but which have undergone biological degradation, for example through storage under damp conditions, or through being left for too long on the beach prior to collection, or also from normal agar manufacture where gel degradation has occurred. The invention can also utilize wastes from high quality agar production but which, for some reason, have undergone degradation and are no longer useful for high gel strength applications. Accordingly this product will be expected to be of considerable value in that it permits the use of material which would otherwise be rejected.

The most straightforward hydrolysis technique is to dissolve the agar in boiling water and add an acidic buffer. After a suitable length of time, which depends on the chosen pH of the solution and the initial gel strength of the agar, the solution is made neutral, and for control purposes this neutralization may include the use of a salt, or acid, which has buffering capacity at around pH7, such as phosphate, and the solution is cooled and allowed to gel. One such acid buffer is sodium hydrogen sulphate, which when 0.125% by weight is added, gives a pH in the order of 1.4, and for an agar with a gel strength of 1000 g/cm$^2$ is reacted at 98 degrees for between 1 minute and 20 minutes, preferably between 5 and 12 minutes, to give a gel with a dynamic gel strength of about 60/g/cm$^2$ (5 minutes) or 10 g/cm$^2$ (10 minutes). Certain polyacids such as citric acid, or pyromellitic acid, can act as an acid buffer for the controlled hydrolysis, and also provide buffering to control the neutralization.

The rate of hydrolysis depends on the strength of the acid. Thus when reacting an identical sample under the same conditions as above, at a pH of 2.6, after one hour the dynamic gel strength was 40 g/cm$^2$, while at pH 4.3, after 1 hr 30 mins, there was no significant loss of gel strength when compared with the original sample. A sample of wet powdered agar, pH of approximately 4.5, was held at 60 degrees for two days, and a material with a dynamic gel strength of approximately 10 g/cm$^2$ was obtained. These times are given as guides for making the product, however the precise times of reaction will be expected to depend to some extent on the nature of the raw material. The method is applicable to agars with methyl ethers. Thus a 1.5% solution of Gracilaria agar which initially had a gel strength of 600 g/cm$^2$, when made acid at pH 1.4 for five minutes at 100 degreees, then neutralized, gave a dynamic gel strength of 30 g/cm$^2$. Similarly, a 1.5% gel made from the alkali treated agar-like extract from Euptilota formosissima, which had a gel strength of 140 g/cm$^2$, when made acid at pH 1.4 for three minutes at 100 degrees, then neutralized, gave a gel with a dynamic gel strength of 10 g/cm$^2$.

The rate of hydrolysis also depends on the concentration of the acid, even though the pH is the same. Thus when 26 g of agar, gel strength 750 g/cm$^2$ were dissolved in 1.5 liters of water at 95 degrees C., the addition of 500 mg of citric acid, following by adjustment of pH to 3.25, gave a gel with dynamic gel strength 40 g/cm$^2$ after 25 minutes, and the creamy material with almost zero dynamic gel strength after 35 minutes. If, on the other hand, the experiment was repeated with 300 mg of citric acid, and the pH adjusted to 3.25, after 35 minutes the gel had a dynamic gel strength of 50 g/cm$^2$.

The exact gel strength obtained is dependent on the specific conditions, and the nature and purity of the agar, and these gel strengths should be considered as examples obtained from this specific set of conditions. It is the method of the invention to obtain a low gel strength agar from the high gel strength material by heating it with an acid catalyst, and a very wide range of possible conditions can be expected within the scope of the invention. Thus for practical reasons the pH range of between 1 and 3.5 would seem to be the most useful, but extremely rapid flash hydrolysis with stronger acid, the use of weaker acids at elevated temperatures in pressurized reactors, or hydrolysis for far longer times with weaker acid is still within the scope of this invention.

Thus if 200 ml if a 15% solution of a slightly coloured agar of gel strength 800 g/cm$^2$ is heated at 118 degrees for 2 hr with 0.4 g sodium bisulphite, which will have a pH initially below 6, a white agar with a dynamic gel strength of about 10 g/cm$^2$ was obtained. The use of pressure will be of particular value if the acid catalyst also functions as a preservative, as in this case the hot solution can be immediately used without further purification, and no isolation of the low gel strength agar is required. Accordingly, all uses of acidic preservatives for the preparation of this low gel strength material are within the scope of this invention provided the end product meets the definition above.

Once the hot solution is prepared, it should be neutralized, eg. by sodium hydroxide or sodium carbonate, and if desirable, the solution can be subjected to chemical reduction, preferably by adding a small amount of sodium borohydride, to remove colour generated from the hydrolysis and stablize the material. Hydrolysis at elevated temperatures using sodium bisulphite will automatically hydrolyse the material and maintain a white colour to the product.

This solution can be used as is, if the sodium sulphate can be tolerated, the sodium sulphate can be removed by means generally known to those practiced in the art, eg by ion exchange, dialysis, washing through ultrafiltration, etc, or the low gelling strength agar can be isolated by means generally known to those practiced in the art, eg direct drying, or through prior concentration, eg through ultrafiltration. A convenient method of concentration is to allow the solution to gel from a reasonably concentrated solution, then to freeze it, then to thaw it and wash/dialyse it in warm water. The agar is readily dialysed, and the solid can be recovered by pouring the solution over a fine mesh and allowing it to drain. Once drained, gentle squeezing will extrude further water. This method has the advantage that it allows easy purification by washing out unwanted salts. However, the method of dewatering the gel can be chosen for convenience, and is not critical to the subject of this invention. It is the ability of the material to be successfully purified by freeze-thawing which partially defines it as being within the scope of this invention.

A further purpose of this invention is to provide uses for these low gel strength agars, and these uses are claimed irrespective of the source of the agar. The low gel strength agar, when cooled from solution, gives a weak gel which can be easily worked to give a paste-like material with unusual consistency and water retention properties. Uses for this material will frequently involve the agar as providing a base material which will carry water, and other materials mixed or dissolved in it.

Thus one novel use for this material is as a base for massage gels. An agar gel obtained by hydrolysis of Pterocladia agar with a dynamic gel strength of approximately 40 g/cm$^2$ is easily worked, and when applied in the course of massage, provides lubrication for a longer period of time than will other gels. We interpret this as being due to the ability of the gel to retain water, and release it slowly through syneresis, although our claim is based on the observed improved performance and not on this explanation. The gel also acts as a carrier for any soluble agent which may give other useful benefits, such as an anti-inflammatory agent, and it will release this more slowly through the course of the massage than would otherwise be the case. It is also possible to add an agent such as a carrageenan or other sulphated polysaccharides from red seaweeds from the Lomentariaceae, Cryptonemiaceae, or Kallymeniaceae families (as defined in "The Marine Algae of New Zealand", V. J. Chapman) to the gel which can be released to give the skin a pleasant rub-out feel following the massage. For a massage gel, the concentration of low gel strength agar should be in the range of 0.5–20% by weight, although the best effects are found in the range of 1–2% by weight. Increasing the concentration of agar increases the stiffness and reduces the overall lubricating power of the gel, but notwithstanding this, increasing the levels of agar up to the 20% range, which would only be practical if the agar is far more hydrolysed than is indicated elsewhere in this patent, are intended to be included in this claim.

A major benefit of the use of these agents as skin application products, including but not limited to, massage gels, is that the resultant product is non-oily, and when rubbed into the skin, leaves no residue which would stain or otherwise adversely affect clothing, and the gels themselves also leave the skin with no visible sign that anything has been applied.

A further use for these low gel strength agars is to produce a mixture which will behave in texture a little like a cream. The material can be easily deformed, or poured, and it behaves as if it had some thixatropic properties. This is particularly the case for those agars at the lowest useful end of their dynamic gel strength, eg from 1–20 g/cm$^2$. It must be emphasised that at these low gel strengths, the "strength" is as much a resistance to flow, and the measurement depends to quite an extent on the velocity of the plunger. The gel strengths quoted here are intended for guidance, and are not intended to be definitive physical measurements.

These very low gel strength agars are expected to have uses as suspending agents, eg to slow the flow of, say, an ice cream topping. Such a topping can, however, take advantage of the hysteresis effect in agar gelation, in that since the gel does not remelt until about 85 degrees C., depending on the source of agar, a topping could also be usefully applied to a hot desert, without it melting and running away as many other such toppings would do. Such a topping could include any normal flavours, including crushed fruit, juice, chocolate flavours, caramels, syrups, and also, taking advantage of the fact that some agars can retain quite high levels of alcohol, liqueurs. It should be emphasised that this invention is that of the base material, and the additives noted here are intended as examples rather than as defining the limits of the usefulness of the material.

The use of such mixture is, of course, not limited to toppings, nor is it limited to desserts. Any food use where a thickened sauce-carrier might be required and where this low gel strength agar is employed is considered within the scope of this invention, and this can include liqueur fillings, fillings for cakes, chocolates, etc, internal sauces for desserts, mayonnaises, etc.

The major advantage for foods that we see in this invention is that it is possible through this invention to make a material of a cream-like texture, but which is neutral, that is it does not react with other foods. Such reactions with other foods can, of course, be useful in themselves, eg the carrageenan-milk reaction is the basis of instant puddings, but equally there are some times in food preparation where a non-interactive food thickener is desirable. This is particularly the case when a range of food mixtures is required, as the thickness of the final product will not depend in any dramatic way as to how the product is made (ie, th e order of addition, which is important with some other food additives) or the nature of the additives. A further advantage lies in the fact that the thickening can be obtained with almost no calories, and totally free of any fat. The only components, besides desired additives, are 98.5% water, or thereabouts, and the remainder an agar which is essentially non-nutritional. Use for preparing diet or diabetic food prepartions is clearly indicated.

While describing this invention, reference has been made to a number of subjective terms to describe texture. The descriptions have been given to assist in outlining the nature of the invention, and such terms are to be regarded solely in this light. The purpose of the invention is to provide the low gelling strength agar as a base for various uses, and is not to be defined by whether such descriptive terms could be used by others.

Where in the foregoing description reference has been made to specific components or integers of the invention having known equivalents, then such equivalents are herein incorporated as if individually set forth.

Although this invention has been described by way of example and with reference to possible embodiments thereof it is to be understood that modifications or improvements may be made thereto without departing from the scope or spirit of the invention.

LITERATURE CITED

R Armisen & F Galatos "Production, Properties and Usage of Agar" FAO Fisheries Technical Paper 288, Chapter 1. FAO, Rome, 1987.

Chapman, V. J., "The Marine Algae of New Zealand", Verlag Von J Cramer 1974

Guiseley, K. B. 1976, U.S. Pat. No. 3,956,273

Furneaux, R., Miller, I. J., Stevenson, T. T. 1990. Hydrobiologia 204/205, 645–654

Kojima, M., Tabata, K., Ukuhashi, P., Ito, Y, 1993 European Patent App. 0 570 252 AZ to Ina Foods Miller, I. J., Falshaw, R., Furneaux, R., 199 Carbohydr Rees 262, 127–135

Rees, D. R., 1969 Adv. Carbohydr. Chem Biochem 24, 267–332.

EXAMPLES

When Pterocladia agar is used in the following examples, the agar had previously been alkali treated, and the sample had a gel strength (1.5% solution) of 750 g/cm$^2$. Other agars were also rigorously alkali treated.

1. 26 g Pterocladia agar was dissolved in 1.4 liters of water at 96 degrees C. 500 mg of citric acid was added and the pH was adjusted to 3.25 by addition of a few drops of dilute hydrochloric acid. The solution was stood at 96 degrees for twenty-five minutes, then the pH was increased to 7 with sodium carbonate solution, 15 mg of sodium borohydride was added, the solution was stirred then poured into containers to gel. The gel was frozen then thawed by immersion in warm water, at which time the agar appeared as a coarse precipitate in the water. The agar was recovered by pouring the liquid onto a gauze, then the agar was dried. On reconstituting, the dynamic gel strength was 40 g/cm$^2$.

2. The procedure of example 1 was followed, except that the solution was at stood at 96 degrees for 35 minutes. This hydrolysed agar could also be isolated from freeze/thawing, and the resultant material, after being recovered from the gauze was placed in a fine cloth and further water pressed from it. The resultant cheese-like material was dried, and on reconstitution by dissolving in hot water (1.5% solids) and cooling gave a cream-like material with zero gel strength.

3. To 1.5 liters of water at 95 degrees was added 22 g of the hydrolysed agar obtained from example 1, then 5 g of *lambda carrageenan* and 1.2 g of commercial bacteriostat. The solution was stirred until dissolution was complete, then the solution was allowed to gel, to give a massage gel base which has good lubrication properties, and when rubbed dry leaves a non-oily smooth feel to the skin.

4. To the hot gel base of example 3, 45 g of the extract from St John's Wort is added and stirred in. When cooled, the gel can be used for massage, while at the same time the essential oil is applied.

5. The procedure of example 3 is followed, except that the hydrolysed agar from example 2 is used. On cooling a gel base is obtained with creamy texture which can be rubbed in and rubbed dry, to give an oil-free skin with a "velvety" feel.

6. The procedures from examples 1 and 2 were followed using agar from *Gracilaria chilensis*, which also started with a gel strength of 700 g/cm$^2$. The final products were similar in gel strength to those quoted in these examples, but the weak gels had a different texture, and tended to release water more quickly when the gel was rubbed than the products from Pterocladia.

7. To the bases of examples 1, 2 and 6 cleansing agents, astringent agents, etc, can be added to allow that function to be completed without leaving an oily residue. Alternatively, small amounts of menthol can be added to give the effect of cooling lotions. The material is applied to the skin the same way a gel or cream is, but on gentle rubbing, it behaves more like a lotion. Thus if 3% of potassium aluminium sulphate and 0.1% bacteriostat are added to a 1.3% solution of the material from example 1, and the solution is allowed to cool, a gel is obtained which when rubbed on the skin behaves in a very similar fashion to an astringent lotion. When dried, gel material is not discernible, and no staining or otherwise objectionable residues remain.

8. The procedures of examples 3 and 5 are followed, but the *lambda carrageenan* is replaced by the extract from *Champia nouvelle-zelandia*. The gel is used for the same purpose, but has the advantage that just prior to rubbing dry, the friction on the skin is much reduced, and the final texture is different. Other sulphated polysaccharides can also be used to replace the carrageenan, each giving slightly different textures and performances.

9. The gel bases can also be used to transport aqueous solutions or emulsions with pharmaceutical or other active ingredients to the skin. Thus a solution was prepared by dissolving 1.3 parts of the material prepared from *Gracilaria chilensis*, according to example 1 0.3 parts fucoidan, and 0.1 parts bacteriostat in 100 parts water and to this was added 3 parts juniper oil dispersed in a mixture of 3 parts of Tween 20 and 3 parts Tween 80. The resultant gel was effective at removing acne, but when applied and rubbed in left no traces of the material which had been applied.

10. Hydrolysates were prepared following the procedures of examples 1 and 2 for the agar from *Curdiea coriaceae*, which has almost two methyl groups per biose unit. 0.67 g of this hydrolysate were dissolved in 50 ml of water containing 0.05 g bacteriostate at 118 degrees in a pressure vessel. The resultant weak gels behave in a similar way to other agars, except that they do not redissolve in boiling water, and they have a different texture.

11. 0.67 g of hydrolysate from *Curdiea coriaceae*, as described in example 10, was heated in a pressure vessel at 180 degrees in the presence of 16 g water. On cooling a syrup was obtained. To this syrup, 48 ml of ethyl alcohol were added carefully with good stirring, the alcohol having been preheated almost to its boiling point. A weak gel similar to those described above is obtained, except that the fluid being carried is 75% alcohol. The alcohol may have essential oils dissolved in it, and may be used as a cooling gel, or as a non-spilling fuel.

12. To 80 g of boiling water was added 1.3 g of the material of example 2 and 0.2 g of preservative, and the liquid was boiled until dissolution was complete. If desired, a thickener, such as *lambda carrageenan* could be dissolved into the solution, and then a fruit essence or concentrate was added. The volume was made up to 100 ml, and the whole allowed to cool, to give a fruit flavoured cream-like material with almost no calories.

Where in the foregoing description reference has been made to specific components or integers of the invention having known equivalents, then such equivalents are herein incorporated as if individually set forth. Although this invention has been described by way of example and with reference to possible embodiments thereof if is to be understood that modifications or improvements maybe made thereto without departing from the scope or spirit of the invention. In particular, since the invention describes a gel for carrying fluids for specific purposes, and where additives known to those familiar with the art are included by way of example, other additives may be used without departing from the scope of the invention.

I claim:

1. A process to manufacture a material able to form an aqueous gel which, at a concentration of 15% of solids by weight has a dynamic gel strength of 0–100 $g/cm^2$, that comprises the sequence of steps of taking an agar or agarose with 0–2 methyl groups per agarobiose unit and which has had the agarobiose content maximised by rigorous alkali treatment such that no increase in gel strength can be achieved by repeated alkali treatment, and dissolving this agar or agarose in water, then partially depolymerizing it by making the pH less than 7 and maintaining temperature between 35–140° C. for a period of time chosen to give the appropriate degree of depolymerization for the required final gel strength, then neutralizing the mixture and cooling it so a gel forms, then freezing then thawing the mixture to provide a particulate solid dispersed in the water, then straining the liquid to obtain the said material.

2. A process to manufacture a material able to form an aqueous gel which, at a concentration of 15% of solids by weight has a dynamic gel strength of 0–100 $g/cm^2$, that comprises the sequence of steps of taking an agar or agarose with 0–2 methyl groups per agarobiose unit and which has had the agarobiose content maximised by rigorous alkali treatment such that no increase in gel strength can be achieved by repeated alkali treatment, and dissolving this agar or agarose in water, then partially depolymerizing it by making the pH less than 7 and maintaining temperature between 35–140° C. for a period of time chosen to give the appropriate degree of depolymerization for the required final gel strength, then neutralizing the mixture and adding sodium borohydride, neutralizing to pH 7, and cooling the mixture so a gel forms, then freezing then thawing the mixture to provide a particulate solid dispersed in the water, then straining the liquid to obtain the said material.

3. The material which is produced by the process of claim 2.

4. A gel for application to skin prepared by redissolving the material produced by the process of claim 1 in hot water and allowing to cool to form said gel.

5. A gel for application to skin prepared by redissolving the material produced by the process of claim 2 in hot water and allowing to cool to form said gel.

6. A gel for application to the skin prepared by redissolving the material produced by the process of claim 1 or claim 2 in hot water together with lambda carrageenan and allowing to cool to form said gel.

7. A gel for application to the skin prepared by redissolving the material produced by the process of claim 1 or claim 2 in hot water together with carrageenans and allowing to cool to form said gel.

8. A gel for application to the skin prepared by redissolving the material produced by the process of claim 1 or claim 2 in hot water together with fucoidan and allowing to cool to form said gel.

9. A gel for application to the skin prepared by redissolving the material produced by the process of claims 1 or claim 2 in hot water together with sulphated polysaccharides from red seaweeds selected from the group consisting of the Lomentariaceae, Cryptonemiaceae, or Kallymeniaceae families and allowing to cool to form said gel.

10. Skin nutritive, emmollient or moisturizing gels prepared by redissolving the material produced by the process of claim 1 or claim 2 in hot water together with nutrient agents and/or agents which maintain moisture levels and allowing to cool to form said gel.

11. Gels for applying insect repellents to the skin prepared by redissolving the material produced by the process of claim 1 or claim 2 in hot water together with insect repellents and allowing to cool to form said gel.

12. Gels for applying pharmaceutical products to the skin prepared by redissolving the material produced by the process of claim 1 or claim 2 in hot water together with pharmaceutical products and allowing to cool to form said gel.

* * * * *